United States Patent [19]

Stiot et al.

[11] 4,013,632
[45] Mar. 22, 1977

[54] WATER INSOLUBLE 6-(2-ACYLOXY-CARBETHOXY) BENZOTHIAZOLE-AZO-BENZENE DYESTUFFS

[75] Inventors: Jean-Pierre Henri Stiot, St. Pierre les Elbeuf; Jean-Marie Louis Leroy, St. Etienne du Rouvray; Claude Marie Henri Emile Brouard, Sotteville les Rouen, all of France

[73] Assignee: Produits Chimiques Ugine Kuhlmann, Paris, France

[22] Filed: June 20, 1974

[21] Appl. No.: 481,440

[30] Foreign Application Priority Data

June 21, 1973, France .................... 73.22695

[52] U.S. Cl. ............................... 260/158; 260/305
[51] Int. Cl.² ................... C09B 29/36; D06P 3/26; D06P 3/48; D06P 2/54
[58] Field of Search ................... 260/158, 157, 152

[56] References Cited

UNITED STATES PATENTS 3,390,145  6/1968  Wippel .................... 260/158

*Primary Examiner*—Daniel E. Wyman
*Assistant Examiner*—John J. Doll
*Attorney, Agent, or Firm*—Beveridge, DeGrandi, Kline, Lunsford

[57] ABSTRACT

Dyestuffs of the formula:

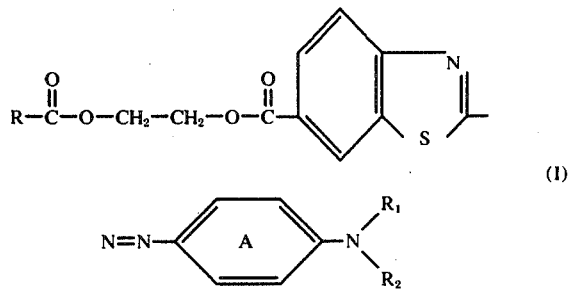

in which R represents a methyl or ethyl group, $R_1$ represents a substituted or unsubstituted alkyl group, $R_2$ represents a hydrogen atom or a substituted or unsubstituted alkyl group, and the benzene nucleus A may be substituted, the molecule being free from groups causing solubility in water by the formation of ions; process for their preparation, process for the coloration of synthetic fibers by means of such dyestuffs, synthetic fibers colored by means of such dyestuffs and diazotizable amines of the formula:

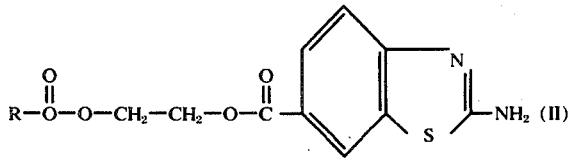

in which R represents a methyl or ethyl group.

3 Claims, No Drawings

WATER INSOLUBLE 6-(2-ACYLOXY-CARBETHOXY) BENZOTHIAZOLE-AZO-BENZENE DYESTUFFS

The present invention relates to new water-insoluble monoazo dyestuffs, which are particularly interesting for the colouration of the synthetic fibres.

According to the present invention water-insoluble monoazo dyestuffs are provided of the general formula:

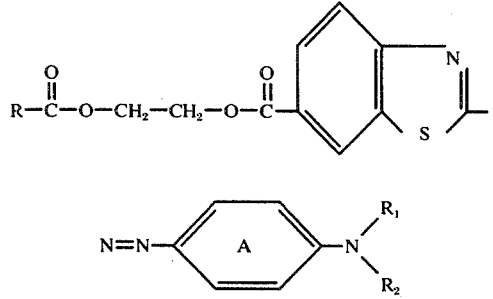
(I)

in which R represents a methyl or ethyl group, $R_1$ represents a substituted or unsubstituted alkyl group, $R_2$ represents a hydrogen atom or a substituted or unsubstituted alkyl group, and the benzene nucleus A may be substituted, the dyestuffs being free from groups causing solubility in water by the formation of ions, such as the free sulphonic acid or carboxylic acid groups.

The alkyl groups represented by $R_1$ and $R_2$ each contain preferably 1 to 4 carbon atoms and each may have one or two substituents, possible substituents of the alkyl groups represented by $R_1$ and $R_2$ are halogen atoms and nitrile, hydroxy, alkoxy, acyl, acyloxy and alkoxycarbonyl groups. The alkoxy groups preferably contain 1 to 4 carbon atoms. The acyl groups are derived from aliphatic carboxylic acids (preferably containing 2 to 5 carbon atoms) or aromatic carboxylic acids (e.g. benzoyl) or araliphatic carboxylic acids (e.g. cinnamoyl). The carbalkoxy groups preferably contain 2 to 5 carbon atoms. Examples of radicals $R_1$ and $R_2$ are methyl, ethyl, propyl, butyl, β-cyanoethyl, β-hydroxyethyl, β,γ-dihydroxypropyl, carbomethoxyethyl, β-acetoxyethyl, β,γ-diacetoxypropyl, methoxyethyl, β-chloroethyl, 2-acetylethyl, β-cinnamoyloxyethyl, and β-benzoyloxyethyl. Examples of radical $R_1$ are 1,2-dimethoxy-carbonyl-ethyl, 1,2-diethoxycarbonyl-ethyl, 2-hydroxy-3-chloro-propyl and 2-acetoxy-3-chloropropyl.

The benzene nucleus A may have 1 or 2 substituents such as, for example, chlorine, methyl, ethyl, methoxy, ethoxy, acetylamino, propionylamino, benzoylamino or cinnamoylamino.

The dyestuffs according to the invention may be prepared for example by coupling the diazo derivative of an amine of the formula:

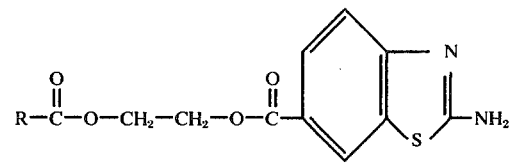
(II)

with a compound of the formula:

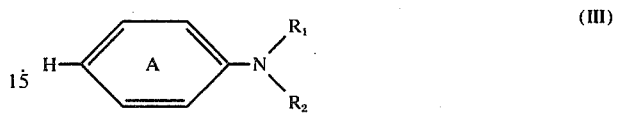
(III)

wherein A, R, $R_1$ and $R_2$ have the meanings given above.

The amines of formula (II) are new products and as such, form part of the present invention. They may be prepared, for example, from amines of the formula:

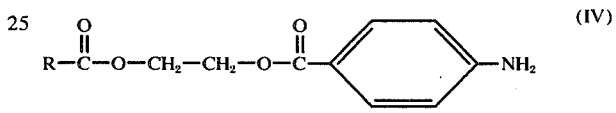
(IV)

described in U.S. Pat. No. 3,663,530 for example by reaction with thiocyanogen and subsequent cyclisation of the β-acyloxyethyl esters of the amino-4-thiocyanato-5-benzoic acid thus obtained.

Examples of coupling components of the formula (III) which may be mentioned are N-ethylaniline, N-propylaniline, N-butyl-aniline, N-ethyl-N-(β-cyanoethyl)-aniline, N,N-bis (β-cyanoethyl)-aniline, N-ethyl-N-(β-hydroxyethyl)-aniline, N,N-bis(β-hydroxyethyl)-aniline, N-ethyl-N-(β-acetoxyethyl)-aniline, N,N-bis(β-acetoxyethyl)-aniline, N-(β-cyanoethyl)-N-(β-acetoxyethyl)-aniline, N-(β-cyanoethyl-N-(β-hydroxyethyl)-aniline, N-ethyl-N-(β-carbethoxyethyl)-aniline, N,N-bis(β-carbethoxyethyl)-aniline, N-(β-cyanoethyl)-N-(β-carbethoxyethyl)-aniline, N-(β-acetoxyethyl)-N-(β-carbethoxy-ethyl)-aniline, N-(β-cyanoethyl)-N-(β-methoxyethyl)-aniline, N-(β-ethoxyethyl)-N-(β-carbethoxyethyl)-aniline, N-ethyl-N-(β-chloroethyl)-aniline, N-propyl-N-(2-acetylethyl)-aniline, N-butyl-N-(β,γ-dihydroxypropyl)-aniline, N-ethyl-N-(β,γ-diacetoxypropyl)-aniline, N-ethyl-N-(β-cyanoethyl)-meta-toluidine, N,N-bis(β-cyanoethyl)-meta-toluidine, N-ethyl-N-(β-acetoxyethyl)-metatoluidine, N-(β-cyanoethyl)-N-(β-acetoxyethyl)-meta-toluidine, N-ethyl-N-(β-carbethoxyethyl)-meta-toluidine, N,N-bis-(β-acetoxyethyl)-meta-toluidine, N-N-bis(β-carbethoxyethyl)-meta-toluidine, N-ethyl-N-(β-carbethoxyethyl)-meta-chloraniline, N-ethyl-N-(β-acetoxyethyl)-meta-chloraniline, N-ethyl-N-cyano-ethyl-meta-chloraniline, N,N-bis(β-acetoxyethyl)-3-acetylamino-aniline, N,N-bis(β-carbethoxyethyl)-3-acetylamino-aniline, N,N-bis(β-acetoxyethyl)-2-methoxy-5-acetylamino-aniline, the dimethyl ester of N-ethyl-N-phenyl-2-amino-succinic acid, and N-ethyl-N-(2-acetoxy-3-chloro-propyl)-aniline.

In a finely divided state, the dyestuffs of formula (I) and, more particularly, those of formula

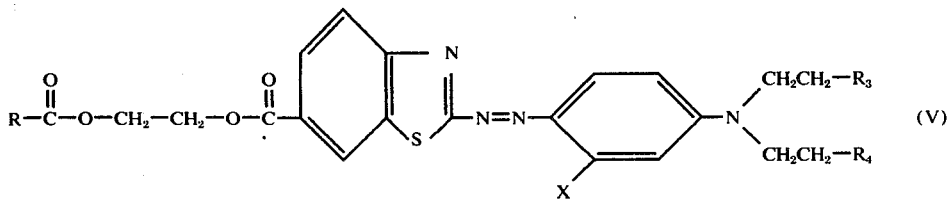

wherein R is as defined above, X represents a hydrogen or chlorine atom, $R_3$ and $R_4$ are identical or different and each represents a chlorine atom or a cyano, hydroxy, alkoxy group containing 1 to 4 carbon atoms, or an acyloxy group containing 2 to 4 carbon atoms, or a carbalkoxy group containing 2 to 4 carbon atoms, $R_4$ also being able to represent a hdyrogen atom are very suitable for the colouration of textiles, such as fibres, yarns, loose fibres, fabrics and knitted goods, based on linear polyesters or cellulose triacetate. Some of them are also very suitable for the colouration of textiles based on acetylcellulose (2½ acetate) or polyamides.

Certain dyestuffs of formula (I) lend themselves to the colouration in bulk of varnishes, oils, synthetic resins and synethetic fibres spun from their solutions in organic solvents.

Further, the compounds of formula (I) are particularly interesting on account of their solubility in the chlorinated hydrocarbons, such as for example trichloroethylene and perchloroethylene, which enables them to be applied in a solvent medium to the polyester fibres.

These new dyestuffs have a good affinity for the abovementioned fibres, which they colour in shades which are fast to light, to combustion gases and to wet tests. In particular, they show a remarkable fastness to sublimation and are in this respect distinctly superior to the similar dyestuffs described in French Pat. No. 1,464,491. It has been surprising to find that this improvement of the fastness to sublimation is not produced to the detriment of the affinity.

The invention is illustrated by the following Examples, in which the parts indicated are parts by weight.

EXAMPLE 1

48 parts of nitrosylsulphuric acid containing 2 parts of nitrous anhydride are run into a mixture of 51 parts of acetic acid and 9 parts of propionic acid, with stirring and while maintaining the temperature at 5° C. 14 parts of the β-acetoxyethyl ester of 2-amino-benzothiazole-6-carboxylic acid are slowly added to the mixture maintained at 5° C., then a mixture of 42.5 parts of acetic acid and 7.5 parts of propionic acid and finally, after 3 hours at 0°–5° C. one adds 2 parts of urea. The clear solution of the diazo derivative thus obtained is then gradually introduced into a mixture of 10.3 parts of N-ethyl-N-cyanoethyl meta-toluidine and 100 parts of acetic acid, while maintaining the temperature at 0°–5° C. by the addition of a little ice. Then 300 parts of a 25% solution of sodium acetate are added, the mixture is stirred for two hours, filtered, and the product washed with water until the washings are neutral and the dyestuff is kneaded with a dispersing agent. It dyes polyester fibres in a red shade, which is very fast, especially to sublimation.

The β-acetoxyethyl ester of 2-amino-benzothiazole-6-carboxylic acid used in this Example may be prepared as follows:

220 parts of the β-acetoxyethyl ester of p-aminobenzoic acid and 333 parts of ammonium thiocyanate are suspended in 1000 parts of acetic acid. The suspension is cooled to 15° C. and then a solution of 176 parts of bromine in 300 parts of acetic acid is gradually added in a period of two hours, without allowing the temperature to exceed 15° C. The mixture is stirred for an hour at 15° C. and then allowed to stand overnight and is subsequently run into 2500 parts of water containing 15 parts of 19° Be hydrochloric acid. Then it is heated to 95° C., filtered at 95° C., and the cooled filtrate is neutralised by the addition of 700 parts of sodium carbonate, filtered again, and the precipitate is washed with 2000 parts of water, drained and dried at 60° C. 215 parts of β-acetoxyethyl ester of 2-amino-benzothiazole-6-carboxylic acid, m.p. 191°–192° C, are thus obtained.

| Elementary analysis | C % | H % | N % | S % |
| --- | --- | --- | --- | --- |
| Calculated for $C_{12}H_{12}N_2O_4S$ | 51.42 | 4.28 | 10 | 11.43 |
| Found | 50.38 | 4.08 | 9.85 | 11.23 |

The following Table summarises other Examples of dyestuffs according to the invention prepared as in Example 1.

| Example | R | Coupling compound of formula (III) | Shade on polyester fibres |
| --- | --- | --- | --- |
| 2 | methyl | N-ethyl-N-(β-cyanoethyl)-aniline | red |
| 3 | '' | N-ethyl-N-(β-cinnamoyloxyethyl)-aniline | '' |
| 4 | '' | N,N-bis(β-acetoxyethyl)-aniline | scarlet |
| 5 | '' | N-(β-hydroxyethyl)-N-(β-cyanoethyl)-aniline | red |
| 6 | '' | N-(β-hydroxyethyl)-N-(β-carbethoxyethyl)-aniline | red |
| 7 | '' | N-(β-hydroxyethyl)-N-(β-methoxyethyl)-aniline | red |
| 8 | '' | N-(β-hydroxyethyl)-N-(β-acetoxyethyl)-aniline | '' |
| 9 | '' | N-(β-cyanoethyl)-N-(β- | |

-continued

| Example | R | Coupling compound of formula (III) | Shade on polyester fibres |
|---|---|---|---|
|  |  | methoxyethyl)-aniline | " |
| 10 | " | N-(β-cyanoethyl)-N-(β-acetoxyethyl)-aniline | scarlet |
| 11 | " | N-ethyl-N-(β-carboethoxyethyl)-aniline | red |
| 12 | " | N-(β-methoxyethyl)-N-(β-carbomethoxyethyl)-aniline | " |
| 13 | " | N-(β-methoxyethyl)-N-(β-acetoxyethyl)-aniline | " |
| 14 | " | N-(β-cyanoethyl)-N-(2-acetylethyl)-aniline | scarlet |
| 15 | " | N-(β-methoxyethyl)-N-(2-acetylethyl)-aniline | red |
| 16 | " | N,N-bis-(β-cyanoethyl)-aniline | scarlet |
| 17 | " | N,N-bis(β-carbethoxyethyl)-aniline | red |
| 18 | " | N-(β-chloroethyl)-N-(β-carbethoxyethyl)-aniline | " |
| 19 | " | N-(β-chloroethyl)-N-(β-methoxyethyl)-aniline | " |
| 20 | ethyl | N-ethyl-N-(β-cyanoethyl)-meta-toluidine | " |
| 21 | methyl | N-ethyl-N-(β-phenoxyethyl) meta-toluidine | red |
| 22 | " | N-ethyl-N-(β-acetoxyethyl)-meta-toluidine | " |
| 23 | " | N-ethyl-N-(β-carbethoxyethyl-meta-toluidine | " |
| 24 | " | N-(β-hydroxyethyl)-N-(β-cyanoethyl)-meta-toluidine | " |
| 25 | " | N-(β-cyanoethyl)-N-(β-acetoxyethyl)-meta-toluidine | red |
| 26 | " | N-(β-acetoxyethyl)-N-(β-carbethoxyethyl)-meta-toluidine | " |
| 27 | " | N-(β-cyanoethyl)-N-(β-carbethoxyethyl)-meta-toluidine | " |
| 28 | " | N,N-bis(β-cyanoethyl)-meta-toluidine | " |
| 29 | " | N,N-bis(β-acetoxyethyl)-meta-toluidine | " |
| 30 | " | N,N-bis(β-carbethoxyethyl)-meta-toluidine | " |
| 31 | " | N-(β-cyanoethyl)-N-(β-methoxyethyl)-meta-toluidine | " |
| 32 | " | N-butyl-N-(β-cyanoethyl)-meta-toluidine | " |
| 33 | " | N-butyl-N-(β-chloroethyl)-meta-toluidine | " |
| 34 | " | N-(β-chloroethyl)-N-(β-methoxyethyl)-meta-toluidine | " |
| 35 | " | N-ethyl-N-(β-carbethoxyethyl)-meta-toluidine | " |
| 36 | " | N-ethyl-N-(β-cyanoethyl)-meta-chloraniline | " |
| 37 | " | N-ethyl-N-(β-hydroxyethyl)-meta-chloraniline | " |
| 38 | " | N-ethyl-N-(β-acetoxyethyl)-meta-chloraniline | " |
| 39 | " | N-ethyl-N-(β-cyanoethyl)-N'-acetyl-metaphenylenediamine | ruby |
| 40 | methyl | N-ethyl-N-(β-hydroxyethyl)-N'-acetyl-meta-phenylenediamine | ruby |
| 41 | " | N-ethyl-N-(β-acetoxyethyl)-N'-acetyl-meta-phenylenediamine | " |
| 42 | " | N-ethyl-N-(β-carbethoxyethyl)-N'-acetyl-meta-phenylenediamine |  |
| 43 | " | N,N-bis(β-hydroxyethyl)-N'-acetyl-meta-phenylenediamine | " |
| 44 | " | N-(β-cyanoethyl)-N-(β-hydroxyethyl)-N'-acetyl-meta-phenylenediamine | " |
| 45 | " | N-(β-cyanoethyl)-N-(β-acetoxyethyl)-N'-acetyl-meta-phenylenediamine | " |
| 46 | " | N,N-bis(β-acetoxyethyl)-5-acetylamino-2-methoxy-aniline | violet |
| 47 | " | N,N-bis(β-hydroxyethyl)-5-acetylamino-2-methoxy-aniline | " |
| 48 | ethyl | N-ethyl-N-(2-acetoxy-3-chloropropyl)-aniline | red |
| 49 | " | dimethyl ester of N-ethyl-N-phenyl-2-amino-succinic acid | " |
| 50 | methyl | N-ethyl-N-(β-acetoxyethyl)-N'-propionyl-meta-phenylenediamine | ruby |
| 51 | " | N-ethyl-N-(β-acetoxyethyl)-N'-benzoyl-meta-phenylenediamine | " |
| 52 | " | N-ethyl-N-(β-acetoxyethyl)-N'- |  |

| Example | R | Coupling compound of formula (III) | Shade on polyester fibres |
|---|---|---|---|
| | | cinnamoyl-meta-phenylenediamine | " |
| 53 | " | N,N-bis-(β-acetoxyethyl)-5-acetylamino-2-ethoxy-aniline | violet |
| 54 | " | N-ethyl-N-(β-acetoxyethyl)-3-ethyl-aniline | red |

We claim:
1. A dyestuff of formula:

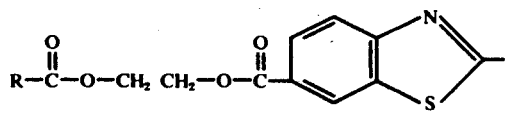

in which
R is methyl or ethyl,
X is hydrogen, chlorine, methyl, ethyl, acetylamino, propionylamino, benzoylamino or cinnamoylamino,
Y is hydrogen, methoxy or ethoxy, $R_1$ is alkyl having 1 to 4 carbon atoms unsubstituted or substituted by one or two chlorine, cyano, hydroxy, alkoxy containing 1 to 4 carbon atoms, acyl containing 2 to 5 carbon atoms, benzoyl, cinnamoyl, acyloxy containing 2 to 5 carbon atoms, benzoyloxy, cinnamoyloxy or carbalkoxy containing 2 to 5 carbon atoms and
$R_2$ is hydrogen or an alkyl group such as $R_1$.

2. Dyestuff of the formula:

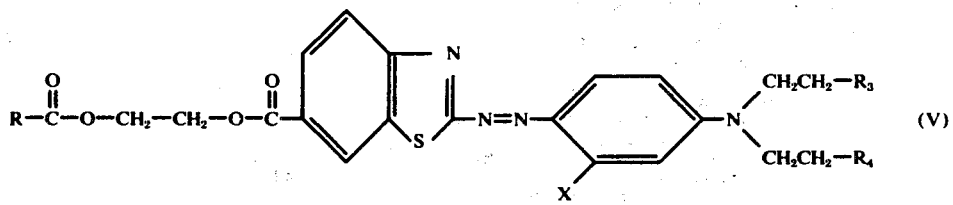

in which
R is methyl or ethyl
X is hydrogen or chlorine
$R_3$ is chlorine, cyano, hydroxy, alkoxy containing 1 to 4 carbon atoms, acyloxy containing 2 to 4 carbon atoms or carbalkoxy containing 2 to 4 carbon atoms and
$R_4$ is hydrogen, chlorine, cyano, hydroxy, alkoxy containing 1 to 4 carbon atoms, acyloxy containing 2 to 4 carbon atoms or carbalkoxy containing 2 to 4 carbon atoms.

3. The dyestuff of formula:

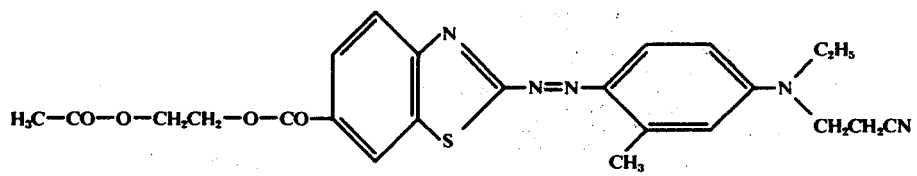

* * * * *